(12) United States Patent
De Smet et al.

(10) Patent No.: US 9,448,206 B2
(45) Date of Patent: Sep. 20, 2016

(54) DEVICE FOR DETECTION OF DEFECTS IN A RECESS

(75) Inventors: Marie-Anne De Smet, Monbrun (FR); Mathieu Berthelot, Lesulis (FR)

(73) Assignee: AIRBUS OPERATIONS S.A.S., Toulouse (FR)

( * ) Notice: Subject to any disclaimer, the term of this patent is extended or adjusted under 35 U.S.C. 154(b) by 204 days.

(21) Appl. No.: 13/526,841

(22) Filed: Jun. 19, 2012

(65) Prior Publication Data

US 2012/0319681 A1 Dec. 20, 2012

(30) Foreign Application Priority Data

Jun. 20, 2011 (FR) ...................................... 11 55397

(51) Int. Cl.
*G01N 27/82* (2006.01)
*G01N 27/90* (2006.01)

(52) U.S. Cl.
CPC .................................. *G01N 27/902* (2013.01)

(58) Field of Classification Search
CPC . G01N 27/82; G01N 27/902; G01N 27/9013
USPC ........................................................ 324/220
See application file for complete search history.

(56) References Cited

U.S. PATENT DOCUMENTS

| | | | |
|---|---|---|---|
| 4,851,773 A | 7/1989 | Rothstein | |
| 5,239,261 A * | 8/1993 | Murdock et al. | 324/750.03 |
| 5,247,251 A | 9/1993 | Yost et al. | |
| 5,465,045 A | 11/1995 | DeRock | |
| 6,076,407 A * | 6/2000 | Levesque et al. | 73/623 |
| 6,112,809 A * | 9/2000 | Angle | 166/66 |
| 7,626,383 B1 * | 12/2009 | Sun et al. | 324/240 |
| 7,683,611 B2 * | 3/2010 | Burkhardt et al. | 324/220 |
| 8,138,755 B2 * | 3/2012 | Drummy | 324/240 |
| 8,264,219 B2 * | 9/2012 | Gibson et al. | 324/220 |

FOREIGN PATENT DOCUMENTS

| | | |
|---|---|---|
| EP | 0 411 874 A2 | 2/1991 |
| EP | 0 411 874 A3 | 2/1991 |

OTHER PUBLICATIONS

French Preliminary Search Report issued Jan. 24, 2012, in Application No. FR 1155397 (FA 754053) (with English Translation of Cited Documents).

* cited by examiner

*Primary Examiner* — Tung X Nguyen
*Assistant Examiner* — Feba Pothen
(74) *Attorney, Agent, or Firm* — Oblon, McClelland, Maier & Neustadt, L.L.P.

(57) ABSTRACT

The invention relates to a device for the detection of defects in a recess, comprising a longitudinal hollow body (107), a movement conversion means (109) housed in said body (107) and installed free to move along the longitudinal direction, and at least one sensor (11) coupled to said body (107) and to said conversion means (109) such that longitudinal translation of the conversion means will move said sensor (11) in transverse translation between a retracted position and an extended position.

14 Claims, 8 Drawing Sheets

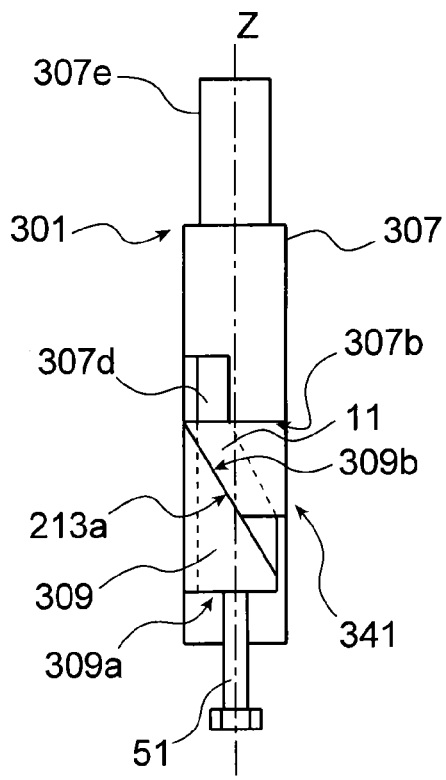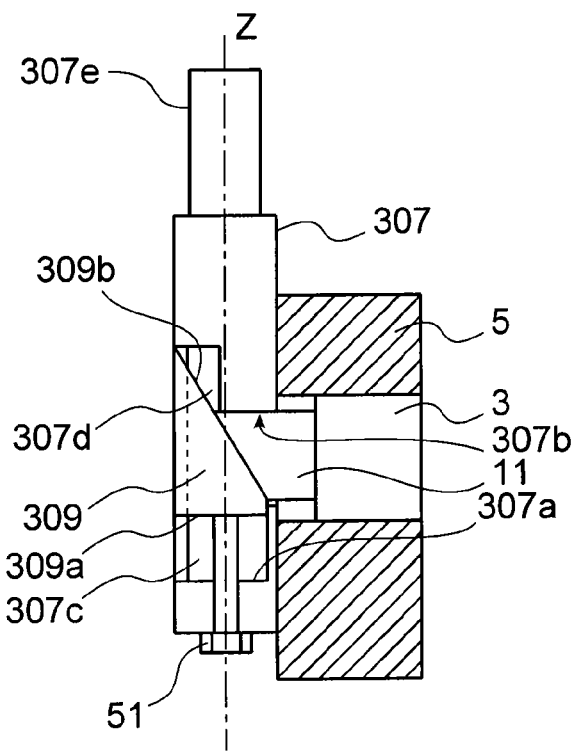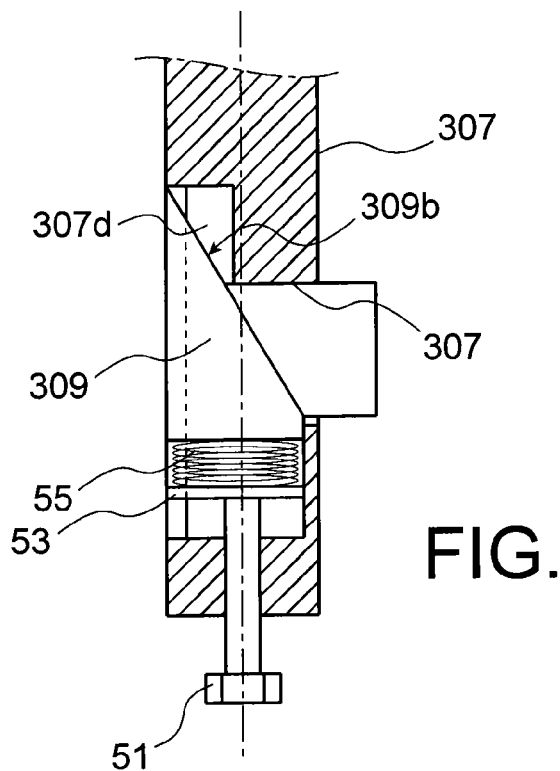

DEVICE FOR DETECTION OF DEFECTS IN A RECESS

TECHNICAL FIELD

This invention relates to the field of devices for the detection of defects in a recess, and more particularly in zones of a recess that are inaccessible or difficult to access.

STATE OF PRIOR ART

Detection of crack, corrosion, delamination type defects or damage in conduits or structures with difficult access creates many problems and frequently requires disassembly of structures. This type of problem occurs in different industrial fields, for example in the oil, nuclear, road and bridges industries and in air, space, and sea transport and other fields.

For example in the airline industry, structures or mechanical parts of aircraft are inspected regularly particularly to detect the presence of cracks or other defects so that appropriate repairs can be made if necessary.

However, some structures or parts may be located in zones to which there is no direct access, for example parts inside an assembly. In some configurations, disassembly of the mechanical parts to be inspected is almost impossible.

Access in other configurations such as wings is possible but difficult for the operator and therefore it can influence the repeatability of the inspection.

There are several ultrasound techniques to reach such zones using a sensor at a distance of a few centimeters from the skin or layer concerned. The path involves reflection of the ultrasounds by successive bounces. However, the geometry of the structure reflects part of the wave in other directions thus reducing the energy level returning to the sensor. This influences the amplitude of the signal characteristic of a crack. These techniques also have strong background noise inducing a false alarm ratio of more than 20%. Furthermore, these techniques are incapable of detecting cracks shorter than about 4 mm and there is an uninspectable dead zone, specifically at the beginning of the curvature of the zone to be inspected.

However, there is another eddy current inspection technique that can detect defects in metallic bodies smaller than 3 mm, or even smaller than 1 mm using rotating sensors.

Detection is done using a sensor that comprises at least one coil through which a variable current passes. When the sensor through which the variable current passes is placed close to a part made from an electrically conducting material, the magnetic flux produced by the coil induces Eddy currents in the part and essentially at the part surface. These Eddy currents in turn create magnetic flux that opposes the generating flux, which modifies the impedance of the coil. Analysis of this impedance variation can detect defects in the part. A defect forms an electrical discontinuity that disturbs the circulation of Eddy currents and creates a variation in the impedance at the coil.

The eddy current detection technique requires displacement of the sensor in the zone of the part to be inspected and defects in the part can be detected by comparing the variation of the impedance of the coil. However, displacement of sensor limits its use to directly accessible zones and the sensor must not be more than 1 mm from the zone to be inspected.

At the present time, defects in zones located in a recess are detected using a sensor like that shown in FIG. 6.

This type of sensor comprises a rod 4 connected to a plate 6 comprising an eddy current sensor 11 located at the edge of the plate 6.

The sensor is inserted into a hole 13 (for example the hole of a removed attachment), and the plate 6 is moved to come into contact with the skin of the recess 3 of the structure 5.

However, this type of sensor can only be used on an assembly for which the diameter of the hole enables insertion of the sensor and its contact with the wall of the recess 3. Furthermore, this type of sensor is incapable of detecting a crack when the radius of the plate 6 is smaller than the distance between the edge of the hole 13 and the surface of the recess 3.

In the field of detection by eddy currents, there is also an extendable rotating sensor that opens when it rotates due to the Coriolis force. However, this type of sensor can only be used in a reaming for which the recess is symmetrical around the entire diameter so that the sensor will not get blocked in its rotation.

The purpose of this invention is to disclose a device for detection of defects in a conduit or in a recess that may be in the structure of an aircraft, a boat or any industrial installation whatsoever and that overcomes the above mentioned disadvantages, particularly in that it can detect all types and sizes of defects (including cracks smaller than or equal to 2 mm), possibly starting from small diameter holes.

PRESENTATION OF THE INVENTION

The purpose of the invention is a device for the detection of defects in a recess comprising:
- a longitudinal hollow body (for example a cylindrical body),
- a movement conversion means housed in said hollow body and installed free to move along the longitudinal direction,
- at least one sensor coupled to said hollow body and to said conversion means such that longitudinal translation of the conversion means will move said sensor in transverse translation between a retracted position and an extended position.

Such a device is capable of precisely detecting defects and particularly all sizes of cracks including cracks smaller than or equal to 2 mm in zones with no direct access in different industrial fields. According to a first embodiment, the conversion means is a rod capable of sliding in the hollow body and the sensor is connected through articulated arms, firstly with the hollow body and secondly with said rod, such that longitudinal translation of said rod extends or retracts the sensor.

According to the first embodiment, the sensor comprises first and second connection points, said first connection point being connected through a first arm to the hollow body and through a second arm to said rod, said second connection point being connected through a third arm to the hollow body and through a fourth arm to said rod.

Advantageously, the second and fourth arms are connected to the rod through a sliding means that can be immobilised on the rod through a first attachment means, said sliding means being capable of adjusting the sensor extension distance as a function of the penetration depth into the recess.

According to a second embodiment, the conversion means is a rod capable of sliding in the hollow body, and the sensor is coupled with said rod through articulated arms and is also guided through an opening defined in the hollow body forming a sliding connection such that the longitudinal translation of said rod causes the extension or retraction of the sensor through said opening.

Advantageously, the detection device according to the first or second embodiment comprises several sensors distributed around the rod.

According to a third embodiment, the conversion means is a pusher with a first straight base and a second oblique base, said pusher being capable of sliding in a complementary-shaped housing delimited on one side by a flat bottom facing the first base and on the other side by a flat ceiling in which there is a cavity facing the second base, said cavity being designed to receive part of said pusher.

The sensor comprises a first inclined side coupled to the second oblique base of the pusher through a first sliding connection and a second straight side bearing on said flat ceiling of the housing and coupled through a second sliding connection to an opening defined in the hollow body such that displacement of the pusher along the longitudinal direction causes transverse displacement of the sensor between the retracted position and the extended position or vice versa through said opening.

Advantageously, the device comprises a screw passing through the flat bottom of the housing to come into contact with said pusher such that rotation of said screw translates said pusher along the axial translation direction.

Advantageously, the device according to any one of the first, second and third embodiments, comprises a frame connected to the hollow body through a pivot link.

This link controls the position and stabilisation of the device and adapt it to several hole widths and several defect positions.

Said at least one sensor comprises coils, a means of activating the coils, and signal processing means to analyse the electrical signals representative of eddy currents at the coils.

Advantageously, the device comprises a data transmission means to transmit data collected through said at least one sensor to a receiver through a wireless link.

BRIEF DESCRIPTION OF THE DRAWINGS

Other characteristics and advantages of the invention will become clear after reading preferred embodiments of the invention, with reference to appended figures among which:

FIGS. 4A-4C diagrammatically show a device for detection of defects according to a third embodiment of the invention;

DETAILED DESCRIPTION OF PARTICULAR EMBODIMENTS

The invention relates to the detection of defects in a recess included in a zone to be inspected. The basic principle of the invention is to use a device composed of a body adapted to be installed in a recess and comprising a sensor and a mechanism to extend the sensor to reach the surface of the recess.

Figure 1:
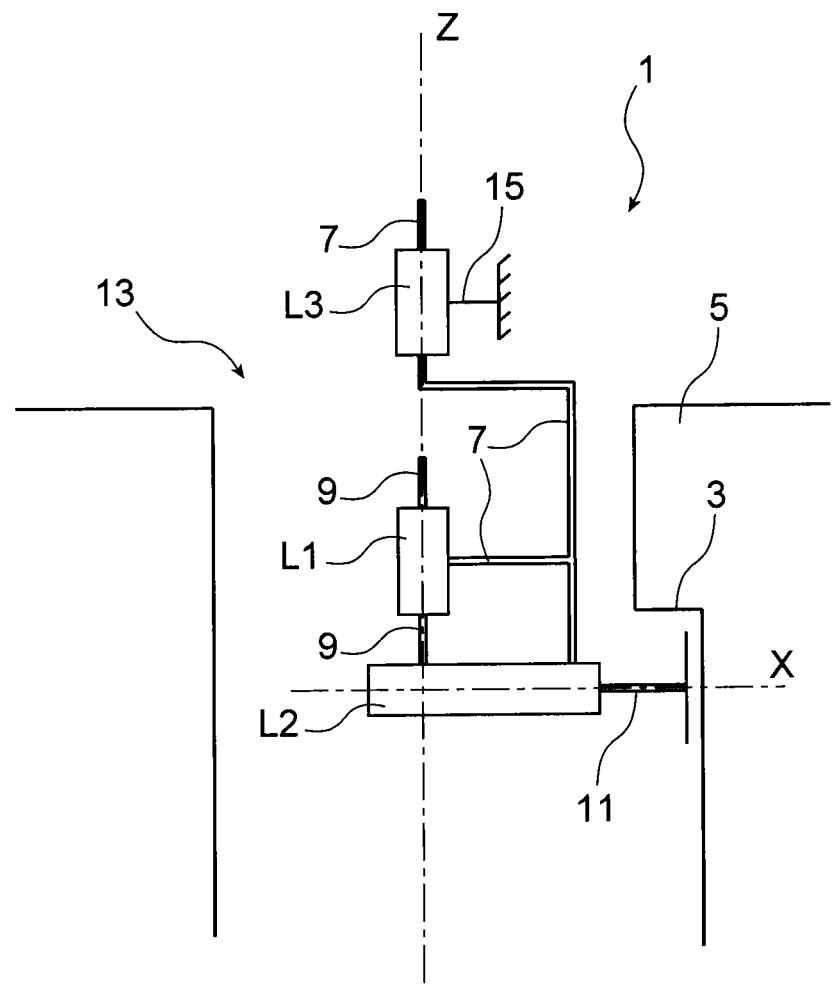
FIG. 1 very diagrammatically shows a device for the detection of defects in a recess according to the invention.

According to the invention, FIG. 1 very diagrammatically shows a device 1 for detection of defects in a recess 3. For example, the recess 3 may be included in a structure 5 composed of an assembly of parts in an aircraft or in any other equipment. This device 1 comprises a longitudinal hollow body 7, a movement conversion means 9 and at least one sensor 11.

The longitudinal hollow body 7 may have an arbitrary section that may be circular or polygonal and adapted to any type of hole or recess. Thus, the longitudinal hollow body 7 may be tubular or cylindrical in shape and designed to be rotated about its Z axis. As a variant, it may be in the shape of a duct with a polygonal cross-section.

The movement conversion means 9 is housed in the hollow body 7 and installed free to move in the longitudinal (or axial) Z direction. In other words, the movement conversion means 9 is coupled to the hollow body 7 through a link L1 free to slide in the longitudinal direction Z. Thus, the body 7 and the conversion means 9 remain fixed to each other if the assembly rotates about the Z axis.

The sensor(s) 11 is (are) coupled through coupling means L2 to the hollow body 7 and to the conversion means 9 such that as the conversion means 9 moves in its longitudinal Z translation, it moves the sensor(s) 11 in transverse (or lateral) X translation between a retracted position and an extended position. The sensor 11 remains fixed in rotation to the movement conversion means 9 and the hollow body 7. Advantageously, a sensor 11 in the retracted position is confined in a space that does not project beyond the lateral surface of the hollow body 7.

Note that the defect sensor 11 may be any sensor among an electromagnetic sensor, air ultrasound sensor, optoelectronic sensor, X or gamma radiation sensor, or any other defect sensor that might be installed on the detection device according to the invention.

Moreover, the defects to be detected may be very varied. For example in metallic structures, defects may comprise cracks or corrosion. Defects in composite materials may comprise delamination or degradation of the resin.

For example, the sensor 11 used to detect cracks in metallic structures of an aircraft may be a high frequency eddy current sensor or magnetic induction sensor. The sensor may comprise one or several coils, placed at the end of the sensor, at least close to the corners of the sensor, or distributed over its entire height to detect an initiating crack or a change to the crack over the height of the recess.

Thus, in order to detect cracks in a layer or a recess 3 in an inspection zone of the structure 5, the device 1 is inserted into a hole 13 in this zone and the conversion means 9 is translated relative to the cylindrical body 7 to extend the sensor(s) 11 until they come into contact with the surface of the recess 3 or the layer concerned. Then, and depending on the configuration of the recess, a longitudinal and/or rotational movement can be applied onto the detection device to scan the surface of the recess 3 or the layer in order to detect cracks.

Furthermore, it can be seen that a sensor can advantageously be composed of a network of eddy current coils for which relative signals are compared with each other in order to create a diagnostic of the surface facing the coils without the need to displace the detection device.

Advantageously, the detection device 1 comprises a frame 15 coupled to the hollow body 7 through a pivot link L3. The frame 15 can be used to fix the device 1 in the zone to be inspected and it may comprise an adjustment means (not shown) to adjust it to the diameters of the hole 13 and the hollow body 7 respectively. As a variant, several different diameter frames 15 can be used to adapt them to different diameter holes 13.

Thus, the frame 15 can be used to stabilise the hollow body 7 and adapt it for several widths of holes 13 and several defect positions. Furthermore, the hollow body 7 may be considered as a half-frame relative to the movement conversion means 9.

For example in the aeronautical field, the diameter of the hollow body 7 (or in other words the diameter of the detection device) is of the order of 6 mm to 12 mm and its length is of the order of 20 mm to 50 mm.

Note that for simplification reasons, the hollow body used in the different embodiments (FIGS. 2A-5B) is non-restrictively shown as a rotating cylindrical body. Obviously, this body may be of any arbitrary cross section as mentioned above.

Figure 2A:
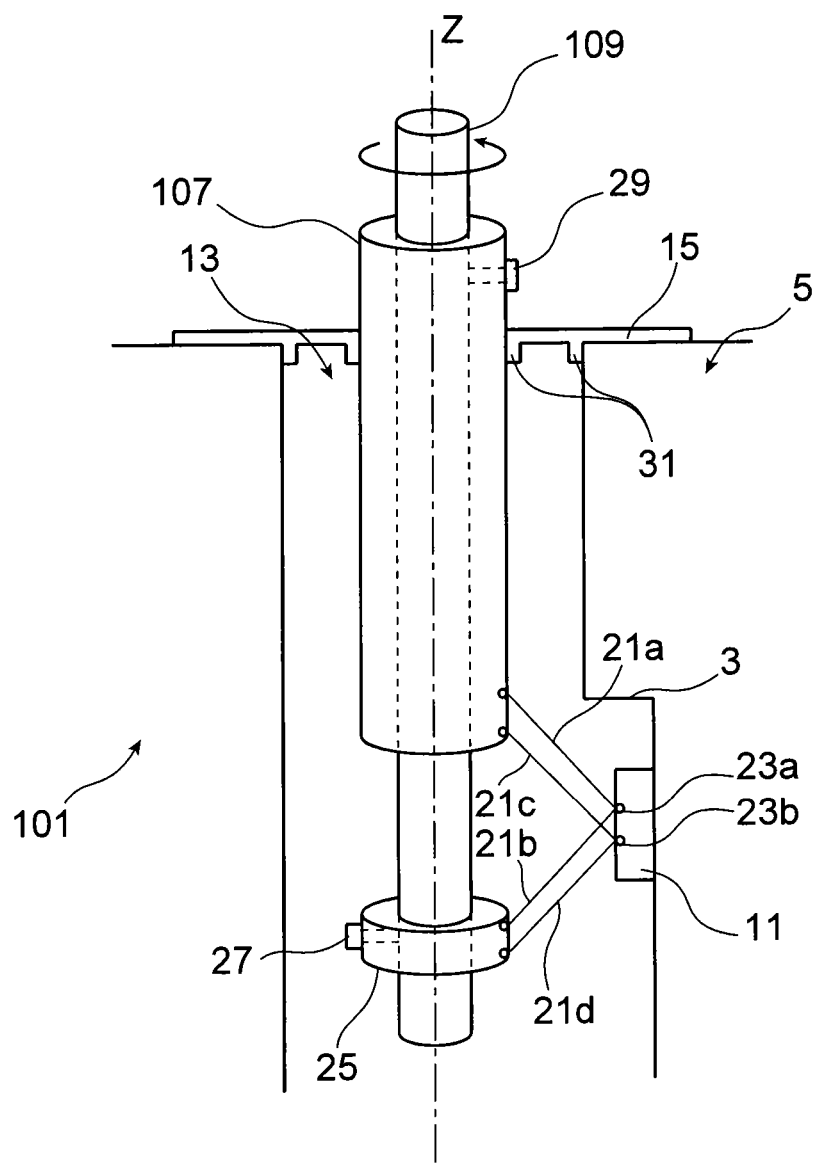
FIGS. 2A-2C diagrammatically show a device for detection of defects according to a first embodiment of the invention.

FIG. 2A diagrammatically shows a defect detection device 101 according to a first embodiment.

According to this first embodiment, the device 101 comprises a longitudinal hollow body 107 (for example a rotating cylindrical body) with open ends, an actuator and a rod 109 that corresponds to the movement conversion means, articulated arms 21a-21d, and at least one sensor 11 (only one sensor is shown in the diagram).

The rod 109 is installed free to slide in the hollow body 107 along a sliding link in the axial direction Z. The sensor 11 is connected through the articulated arms 21a-21d firstly with the hollow body 107 and secondly with the rod 109 such that the axial translation of the rod 109 will extend or retract the sensor 11, by an "umbrella effect".

More particularly, the sensor 11 comprises first and second connection or link points 23a, 23b. The first connection point 23a is connected through a first arm 23a to the hollow body 107 and through a second arm 21b to the rod 109. The second connecting point 23b is connected through a third arm 21c to the hollow body 107 and through a fourth arm 21d to the rod 109. Thus, the first and second arms 21a, 21b are connected to the same first connecting point 23a and the third and fourth arms 21c, 21d are connected to the same second connecting point 23b, so that the sensor 11 will remain always in the vertical Z direction. Furthermore, the first and third arms 21a, 21c (upper arms) are parallel to each other and the second and fourth arms 21b, 21d (lower arms) are also parallel to each other, to achieve precise and stable guidance. For example, the arms 21a-21d may be connected to the hollow body 107, to the rod 109 and to the sensor 11 through pivot connections.

The second and fourth arms 21b, 21d (lower arms) may be connected directly or indirectly to the rod 109.

Advantageously, the second and fourth arms 21b, 21d are connected to the rod 109 through a sliding means 25. For example, if the rod 109 is cylindrical in shape, the sliding means 25 is in the form of a ring that can slide along the rod 109 in order to adjust the maximum extension distance of the sensor 11. Once the position of the sliding means 25 has been adjusted, it can be immobilised or fixed on the rod 109 by a first fixing or attachment means 27 (for example a screw). Thus, the sliding means 25 can be used to precisely position the maximum extension position necessary to reach the zone to be inspected.

Furthermore, the device 101 comprises a second adjustment or attachment means 29 (for example a screw) to adjust the position of the rod 109 relative to the hollow body 107 at a precise height as a function of the extended configuration necessary to reach the surface of the recess 3. This second attachment means 29 can fix the outer body 107 in position relative to the rod 109 to stabilise the sensor 11 after it has been extended.

Thus, when the rod 109 is in the down position, the arms 21a-21d are folded along the rod 109 and the sensor 11 is retracted. On the other hand, when the rod 109 is raised in axial translation, the arms 21a-21d move away from the rod 109 to extend the sensor 11. Translation of the rod 109 along the opposite direction returns the sensor 11 into its retracted position.

Operation of the device 101 can be illustrated by placing the frame 15 at the hole 13 in the zone to be inspected. The adjustment means 31 of the frame 15 is used to adjust the frame 15 relative to the clearance between the reaming and the hollow body 107 so as to stabilise the detection device 101. The frame 15 is used to keep the detection device on a central position if the diameter of the hollow body 107 is less than the diameter of the hole 13. When the rod 109 is in the down position (in other words sensor retracted) and the sliding means 25 is fixed on the rod 109, the device 101 is inserted into the hole 13 and the rod 109 is raised until the height of the zone to deploy the sensor 11 is reached approximately, so that the sensor comes into contact with the surface of the recess 3 and the rod 109 is then fixed relative to the hollow body 107 using the second attachment means 29. Then, if the hollow body 107 is cylindrical in shape, the assembly is rotated (either manually or with a stepping motor) to scan the zone at the chosen height.

Note that the connection points 23a, 23b on the sensor 11 may be arranged to access corners of the recess 3.

Figure 2B:
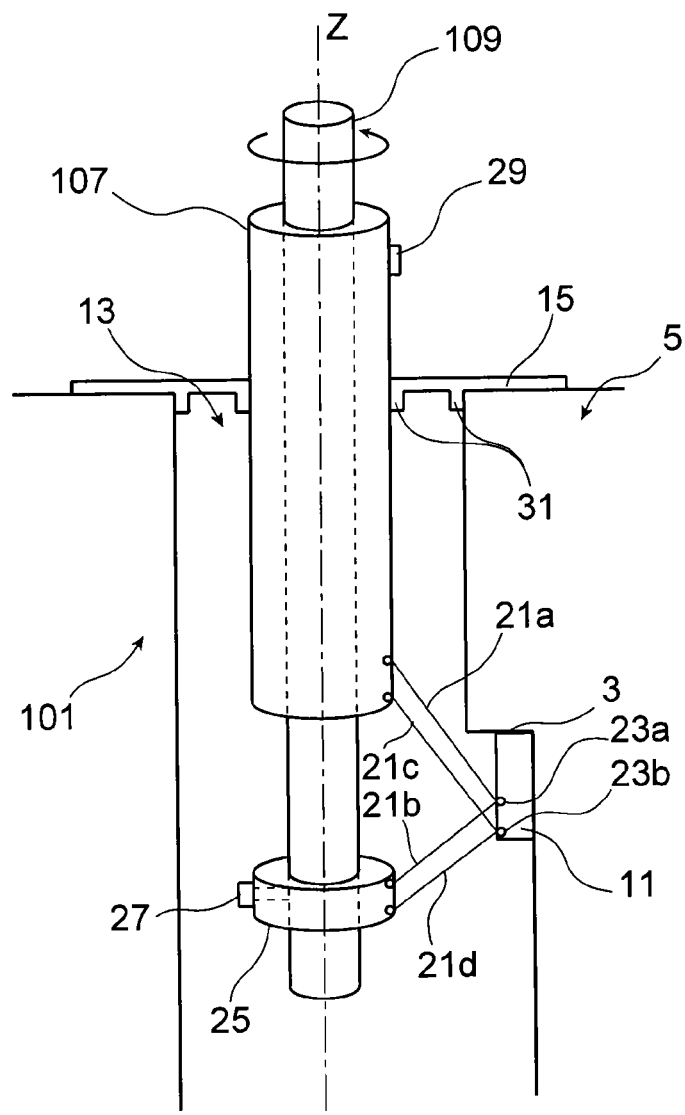

For example, FIG. 2B diagrammatically shows a detection device 101 according to the first embodiment with connection points 23a, 23b located in the lower part of the sensor 11. This makes it possible to insert the sensor 11 upwards to access the upper corners of the recess 3 without being hindered by the inclination of the arms 21a-21d.

Similarly, the connection points may be located in the upper part of the sensor 11 so that the sensor can access the lower corners of the recess 3.

Figure 2C:
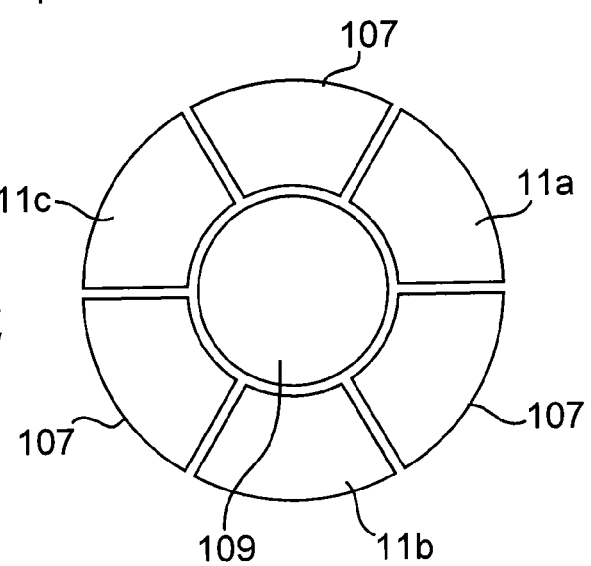

FIG. 2C diagrammatically shows a top view of a detection device 101 according to the first embodiment.

In this example, the device 1 comprises three sensors 11a, 11b, 11c distributed at uniform intervals around the rod 109. The dimensions of the sensors 11a-11c are defined such that when they are in the retracted position, the sensors 11a-11c do not project beyond the outside contour of the hollow body 107.

The detection device 101 according to the first embodiment can be used to access the recess 3 from only one side of the structure. Furthermore, the sensor(s) 11a-11c can be extended to a distance equal to several times the diameter of the hollow body 107. Thus, surfaces of a recess 3 can be inspected even at a distance very much greater than the nominal diameter of the hole 13. Furthermore, the device 101 can be used to detect cracks in a recess 3 with an arbitrary or random geometric shape.

Figure 3A:
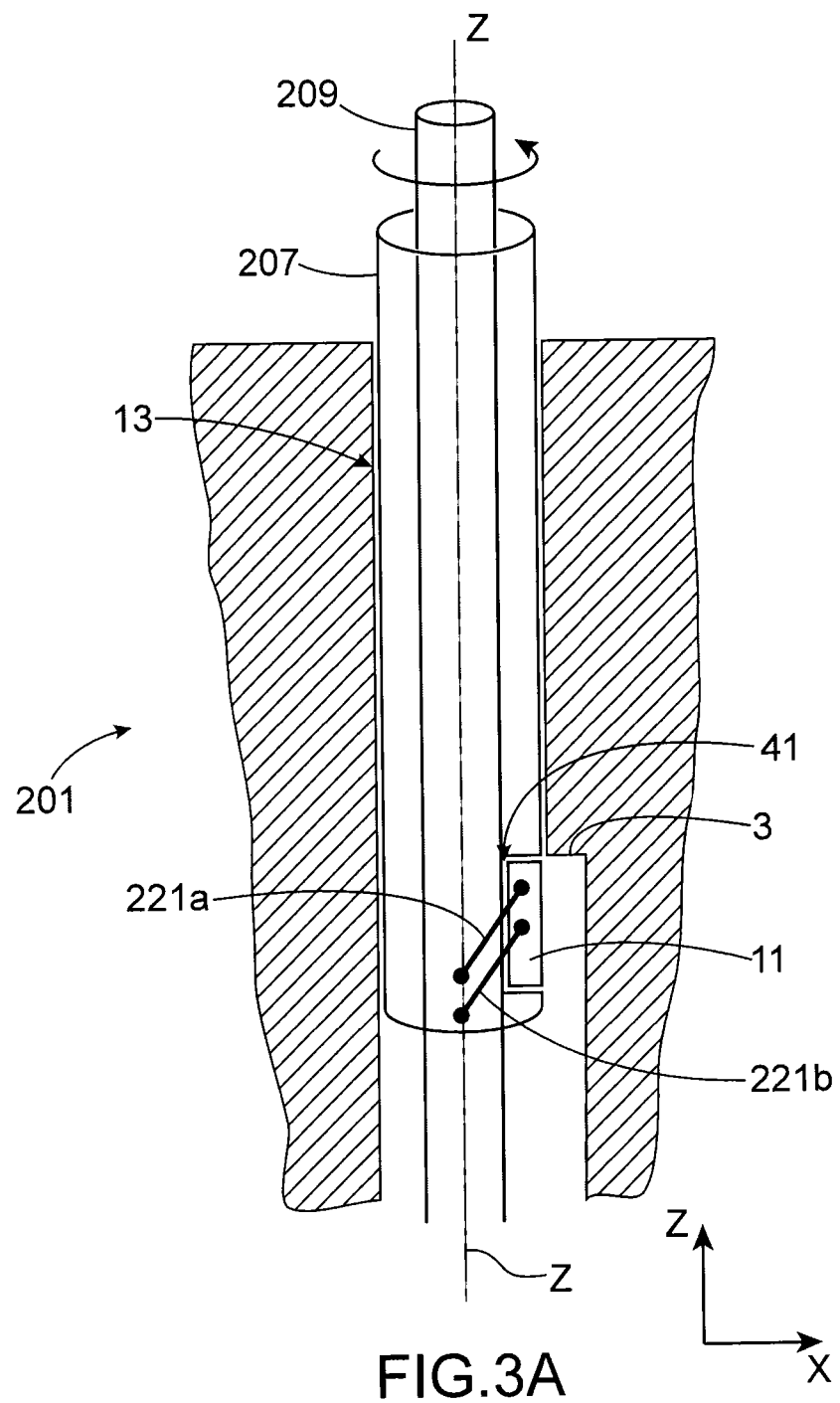
FIGS. 3A and 3B diagrammatically show a device for detection of defects according to a second embodiment of the invention.
Figure 3B:
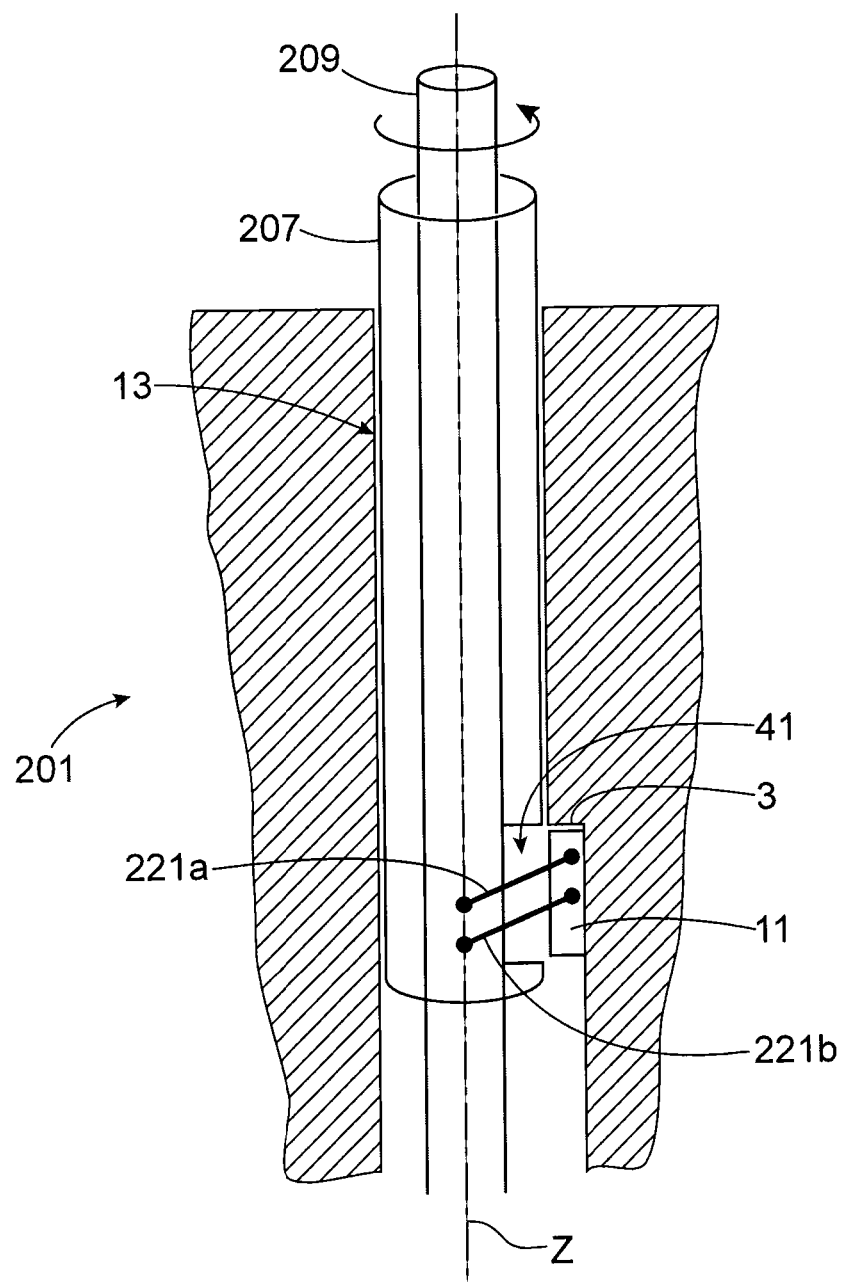

FIGS. 3A and 3B diagrammatically show a defect detection device 201 according to a second embodiment.

According to this second embodiment, the device 201 comprises a hollow body 207 (for example cylindrical in shape) with open ends and with at least one side opening 41 (in this case only a single side opening is shown), an actuator or a rod 209 that corresponds to the movement conversion means, articulated arms 221a, 221b, and at least one sensor 11. FIGS. 3A and 3B show a device with a single sensor 11 but obviously the device may comprise several sensors distributed around the rod 209.

The rod 209 is installed free to move in the hollow body 207 along a link free to slide in the longitudinal (or axial) Z direction to slide in the hollow body 207. The sensor 11 is coupled firstly with the rod 209 by articulated arms 221a, 221b and secondly it is guided by the opening 41 defined in the hollow body 207 forming a sliding connection. Thus, axial translation of the rod 209 extends or retracts the sensor 11 through the opening 41.

With this example, the sensor 11 is coupled to the rod 209 through the two arms 221a, 221b according to the pivot links.

Thus, when the rod 209 is in the down position, the arms 221a, 221b are folded along the rod 209 and the sensor 11 is retracted into its housing (see FIG. 3A). On the other hand, when the rod 209 is in the up position, the arms 221a, 221b are extended to create contact between the sensor 11 and the recess 3 (see FIG. 3B).

More particularly, when the rod 209 is raised from its down position, the arms 221a, 221b will tend to push the sensor 11 and the sensor will extend transversely or horizontally (X direction) along the sliding connection formed by the opening 41 in the hollow body 207. Conversely, when the rod 209 is lowered from its up position, the arms 221a, 221b will tend to pull the sensor 11 and the sensor will fold horizontally (X direction) always along the sliding connection formed by the opening 41 in the cylindrical body 207. Thus, according to this configuration, the sensor 11 can extend as far as a distance slightly less than the radius of the hollow body 207. The device 201 according to this second embodiment can easily access the corners of the recess 3.

FIGS. 4A and 4B diagrammatically show a defect detection device 301 according to a third embodiment.

According to this third embodiment, the device 301 comprises a hollow body 307 (for example cylindrical in shape) with a side opening 341, a pusher or piston 309 (for example cylindrical in shape) that corresponds to the movement conversion means, and a sensor 11.

The pusher 309 has a first straight base 309a (in other words a plane base perpendicular to the axial Z direction) and a second oblique base 309b (in other words a plane base inclined from the axial direction). The pusher 309 is installed free to move in the hollow body 307 by means of a sliding connection to slide along the axial Z direction in a complementary-shaped housing 307c. The housing 307c is delimited on one side by a flat bottom 307a facing the first base 309a of the pusher 309 and on the other side by a flat ceiling 307b provided with a cavity 307d facing the second base 309b of the pusher 309. The cavity 307d will hold a part of the oblique base 309b of the pusher 309.

The sensor 11 is coupled firstly to the pusher 309 through a first link free to slide along a direction inclined from the longitudinal (or axial) Z direction, and secondly to the hollow body 307 through a second link free to slide along a direction perpendicular to the axial Z direction.

The sensor 11 comprises a first inclined side (at the same inclination as the oblique base of the pusher) and a second straight side. The first inclined side of the sensor 11 is coupled to the second oblique base 309b of the pusher 309 forming the first sliding connection. The second straight side of the sensor 11 bears on the flat ceiling 307b of the housing 307c and is guided through the opening 341 defined in the hollow body 307 to form the second sliding connection. Thus, displacement of the pusher 309 along the longitudinal Z direction causes the sensor 11 to move transversely between the folded position (FIG. 4A) and the extended position (FIG. 4B) or vice versa through the opening 341.

The cylindrical pusher 309 may be translated longitudinally or axially by a transmission means 51 to push or pull the pusher 309.

For example, the device 301 comprises a screw 51 passing through the flat bottom 307a of the housing 307c to come into contact with the pusher 309 such that rotation of the screw 51 in one direction or another will cause axial translation of the pusher 309 in a corresponding direction.

Advantageously, the device 301 comprises a branch 307e integrated into the hollow body 307 on the end opposite to the end with the screw 51. For example, the branch 307e can rotate the device 301 or move it axially to scan the zone to be inspected.

Thus by firstly turning the screw 51 in the clockwise direction, the pusher 309 is pushed upwards and in turn it will push the sensor 11 through the opening 341 to come into contact with the surface of the recess 3. Then, by rotating or moving the device 301 in the axial direction through the branch 307e integrated into the hollow body, the sensor 11 can scan the zone to detect defects. When the screw 51 is rotated in the opposite direction, the pusher 309 moves downwards again, bringing the sensor 11 back inside the cylindrical body 307.

FIG. 4C diagrammatically shows a defect detection device 303 according to a variant of the third embodiment.

According to this variant, the screw 51 passing through the flat bottom of the housing 307c is in contact with the pusher 309 through a plate 53 fitted with a spring 55. The plate 53 that may be circular in shape can distribute the force output from the screw 53 uniformly over the flat base 309a of the pusher 309 and the spring 55 applies a pressure force to maintain the sensor 11 in contact with the surface of the recess 3.

Thus, either of the variants can be used depending on the geometry of the recess 3.

The variant in FIG. 4C can advantageously be used for random-shaped local recesses because the sensor 11 remains in contact with the surface of the recess 3 due to the pressure applied by the spring 55.

The variant in FIG. 4A can be used for symmetrical-shaped recesses because the force applied by the screw 51 is sufficient to keep the sensor 11 in contact with the surface to be inspected.

Note that the hollow body in the different embodiments according to the invention can be rotated either by hand or automatically with an electric motor, depending on the geometry of the recess. For a random-shaped recess, if the device 301 needs to be rotated, it will be done slowly and manually so that the sensor 11 can be adjusted to match an edge or an undulation on the surface to be inspected.

Figure 5A:
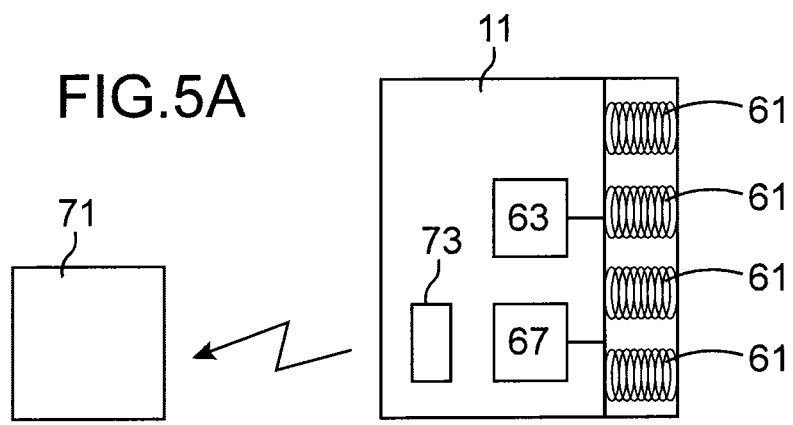
FIGS. 5A and 5B diagrammatically show sensors 11 that can be used in the detection device according to any one of the embodiments of the invention.
Figure 5B:
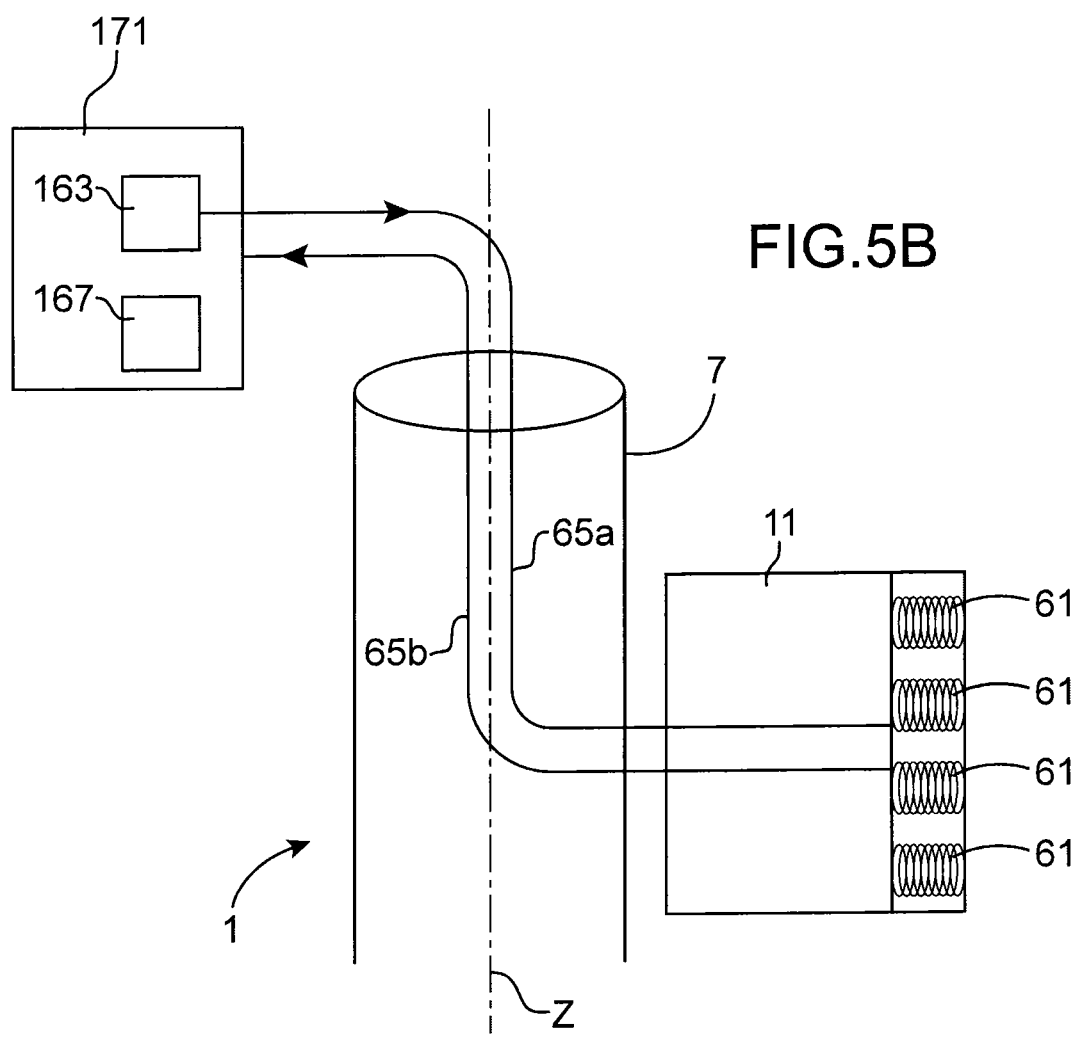
Figure 6:
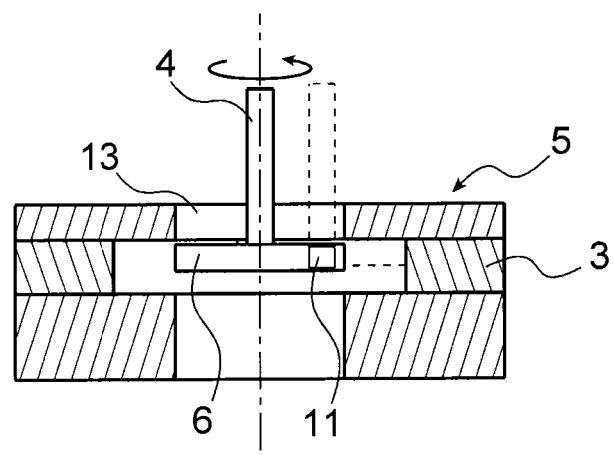
FIG. 6 diagrammatically shows a device for the detection of defects according to prior art.

FIGS. 5A and 5B diagrammatically illustrate sensors 11 that can be used in the detection device according to any of the different embodiments. The sensor may be an electromagnetic, ultrasound, optoelectronic, X-ray type sensor, etc.

For example, the sensor 11 may be an eddy current sensor with a network of small detection coils 61. The coils 61 may be connected in parallel, so that they can be processed individually as a plurality of eddy current detectors. For example, the diameter of each coil 61 may be about 0.5 mm to 1 mm and its height of about 1 mm to several mm. Thus, the coil diameter may be adapted to the smallest defect to be detected, usually of the order of 1 mm, and can even detect cracks smaller than 1 mm. Furthermore, depending on the height of the coils, the sensor 11 can detect defects at several depths relative to the surface to be inspected.

The coils 61 are individually activated by an actuation means 63 such as a pulse generator. This generator applies power to the coils 61 at an excitation frequency that can be chosen as a function of parameters related to the material of the structure, for example such as its electrical conductivity, its magnetic permeability and the geometric shape and thickness of the structure, etc.

Advantageously, the activation means 61 may be placed inside the sensor 11 (FIG. 5A) or the detection device. As a variant, the activation means 163 may be placed outside the detection device 1, and in this case it is connected to the coils 61 through an electrical wire 65a passing through the axis of the hollow body 7.

Furthermore, the sensor 11 may comprise a signal processing means 67 to analyse electrical signals representative of eddy currents at the coils 61 in order to detect cracks (FIG. 5A). As a variant, signal processing may be exported to a signal processing system 167 external to the device (FIG. 5B).

Note that information output from the sensor 11 may be transmitted to a reception device 171 or 71 through a wire link 65b (FIG. 5B) or a wireless link (FIG. 5A). In the second case, the sensor 11 comprises a data transmission means 73 to transmit data collected by the sensor 11 to the receiver 71 through a wireless link.

The invention claimed is:

1. A device for detection of defects in a recess, wherein said device comprises:
   a longitudinal hollow body,
   a movement converter housed in said hollow body and installed free to move along a longitudinal direction of the hollow body, and
   at least one sensor to detect one or more of the defects in the recess and coupled to said hollow body and to said converter such that longitudinal translation of the converter is configured to move said at least one sensor in transverse translation between a retracted position and an extended position, wherein
   the hollow body and the converter are rotatable around the longitudinal direction of the hollow body to rotate the at least one sensor.

2. The device according to claim 1, wherein the converter is a rod that is slidable in said hollow body, and wherein the at least one sensor is connected through articulated arms firstly with the hollow body and secondly with said rod such that longitudinal translation of said rod extends or retracts the at least one sensor.

3. The device according to claim 2, wherein the at least one sensor comprises first and second connection points, said first connection point being connected through a first arm to the hollow body and through a second arm to said rod, said second connection point being connected through a third arm to the hollow body and through a fourth arm to said rod.

4. The device according to claim 3, wherein the second and fourth arms are connected to the rod through a sliding mechanism that can be immobilised on the rod through a first attachment mechanism.

5. The device according to claim 2, further comprising a second attachment mechanism to adjust the position of the rod relative to the hollow body.

6. The device according to claim 1, wherein the converter is a rod that is slidable in the hollow body, and wherein the at least one sensor is coupled firstly with said rod through articulated arms and secondly is guided through an opening defined in the hollow body forming a sliding connection such that the longitudinal translation of said rod causes the extension or retraction of the at least one sensor through said opening.

7. The device according to claim 2, further comprising several sensors distributed around the rod.

8. The device according to claim 1, wherein the converter is a pusher with a first straight base and a second oblique base, said pusher being slidable in a complementary-shaped housing delimited on one side by a flat bottom facing the first base and on the other side by a flat ceiling in which there is a cavity facing the second base, said cavity being designed to receive part of said pusher.

9. The device according to claim 8, wherein the at least one sensor comprises a first inclined side coupled to the second oblique base of the pusher through a first sliding connection and a second straight side bearing on said flat ceiling of the housing and coupled through a second sliding connection to an opening defined in the hollow body such that displacement of the pusher along the longitudinal direction causes transverse displacement of the at least one sensor between the retracted position and the extended position or vice versa through said opening.

10. The device according to claim 8, further comprising a screw passing through the flat bottom of the housing to come into contact with said pusher such that rotation of said screw translates said pusher along the axial translation direction.

11. The device according to claim 1, further comprising a frame connected to the hollow body through a pivot link.

12. The device according to claim 1, wherein said at least one sensor comprises coils, an apparatus that activates the coils and a signal processor to analyze the electrical signals representative of eddy currents at the coils.

13. The device according to claim 1, further comprising a data transmitter to transmit data collected through said at least one sensor to a receiver through a wireless link.

14. A device for detection of defects in a recess, wherein said device comprises:
   a longitudinal hollow body,
   a movement converter housed in said body and installed free to move along the longitudinal direction, and
   at least one sensor coupled to said body and to said converter such that longitudinal translation of the converter is configured to move said sensor in transverse translation between a retracted position and an extended position, wherein
   the converter is a pusher with a first straight base and a second oblique base, said pusher being slidable in a complementary-shaped housing delimited on one side by a flat bottom facing the first base and on the other side by a flat ceiling in which there is a cavity facing the second base, said cavity being designed to receive part of said pusher, and wherein
   the at least one sensor comprises a first inclined side coupled to the second oblique base of the pusher through a first sliding connection and a second straight side bearing on said flat ceiling of the housing and coupled through a second sliding connection to an opening defined in the hollow body such that displacement of the pusher along the longitudinal direction causes transverse displacement of the at least one sensor between the retracted position and the extended position or vice versa through said opening.

* * * * *